(12) United States Patent
Goldman

(10) Patent No.: US 8,408,903 B2
(45) Date of Patent: Apr. 2, 2013

(54) MULTI-CORTICAL DENTAL IMPLANT ANCHOR, DENTAL IMPLANT KIT AND TEMPLATE

(76) Inventor: Serge Goldman, Jerusalem (IL)

( * ) Notice: Subject to any disclaimer, the term of this patent is extended or adjusted under 35 U.S.C. 154(b) by 641 days.

(21) Appl. No.: 11/658,648

(22) PCT Filed: Sep. 28, 2005

(86) PCT No.: PCT/IL2005/001046
§ 371 (c)(1),
(2), (4) Date: Jan. 26, 2007

(87) PCT Pub. No.: WO2006/038209
PCT Pub. Date: Apr. 13, 2006

(65) Prior Publication Data
US 2009/0004626 A1 Jan. 1, 2009

(30) Foreign Application Priority Data

Oct. 3, 2004 (IL) .......................................... 164374
Mar. 14, 2005 (IL) .......................................... 167421

(51) Int. Cl.
*A61C 8/00* (2006.01)
(52) U.S. Cl. ...................................................... 433/173
(58) Field of Classification Search .......... 433/172–176, 433/201.1, 75–76; 623/16.11, 17.17; 411/522; 606/310, 75, 151, 157, 219, 220, 232
See application file for complete search history.

(56) References Cited

U.S. PATENT DOCUMENTS

| 2,364,880 | A | * | 12/1944 | Tinnerman | 411/527 |
|---|---|---|---|---|---|
| 3,436,826 | A | * | 4/1969 | Edelman | 433/75 |
| 3,579,829 | A | * | 5/1971 | Sampson | 433/158 |
| 3,919,772 | A | * | 11/1975 | Lenczycki | 433/173 |
| 4,203,218 | A | | 5/1980 | Dal Pont | |
| 4,325,373 | A | * | 4/1982 | Slivenko et al. | 606/96 |
| 4,379,694 | A | * | 4/1983 | Riess | 433/201.1 |
| 4,521,192 | A | * | 6/1985 | Linkow | 433/173 |
| 4,762,492 | A | * | 8/1988 | Nagai | 433/174 |
| 4,828,492 | A | * | 5/1989 | Agnone | 433/173 |
| 5,306,149 | A | | 4/1994 | Schmid et al. | |
| 5,439,381 | A | * | 8/1995 | Cohen | 433/173 |
| 5,513,989 | A | * | 5/1996 | Crisio | 433/176 |
| 6,450,812 | B1 | * | 9/2002 | Laster et al. | 433/173 |
| 2007/0105068 | A1 | * | 5/2007 | Stucki-McCormick | 433/173 |

FOREIGN PATENT DOCUMENTS

| DE | 4223153 | 1/1993 |
|---|---|---|
| JP | 02-063454 | 2/1990 |
| JP | 05-253247 | 10/1993 |

OTHER PUBLICATIONS

International Preliminary Report on Patentability Dated Oct. 30, 2006 From the International Preliminary Examining Authority Re.: Application No. PCT/IL05/01046.

(Continued)

*Primary Examiner* — Yogesh Patel

(57) ABSTRACT

A multi-cortical implant anchor for use with a dental implant having a generally elongate shank and a grippable region formed at a predetermined portion thereof, the implant anchor comprises a first elongate member and a second elongate member connected therebetween via a bridge member to generally form a member having a longitudinal axis, the first elongate member and the second elongate member being adapted to lockably engage the grippable region of the dental implant against pivoting in a direction transverse to the longitudinal axis.

24 Claims, 7 Drawing Sheets

OTHER PUBLICATIONS

International Search Report Dated May 31, 2006 From the International Searching Authority Re.: Application No. PCT/IL05/01046.
Response Dated Nov. 15, 2009 to Office Action of Jul. 24, 2009 From the State Intellectual Property Office of the People's Republic of China Re.: Application No. 200580041319.8.
Translation of Office Action Dated Jul. 24, 2009 From the State Intellectual Property Office of the People's Republic of China Re.: Application No. 200580041319.8.
Written Opinion Dated May 31, 2006 From the International Searching Authority Re.: Application No. PCT/IL05/01046.
Response Dated Apr. 25, 2010 to Office Action of May 25, 2008 From the Israel Patent Office Re.: Application No. 167421.
Translation of Notice of Reasons for Rejection Dated Oct. 29, 2010 From the Japanese Patent Office Re. Application No. 2007-534177.
Office Action Dated Mar. 10, 2011 From the Israel Patent Office Re.: Application No. 167421 and Its Translation Into English.
Examiner's Report Dated Jun. 24, 2010 From the Australian Government, IP Australia Re. Application No. 2005290847.
Requisition by the Examiner Dated Jan. 12, 2012 From the Canadian Intellectual Property Office Re. Application No. 2,582,393.
Translation of Office Action Dated Dec. 21, 2011 From the State Intellectual Property Office of the People's Republic of China Re.: Application No. 200580041319.8.
Office Action Dated May 25, 2008 From the Israel Patent Office Re.: Application No. 167421.

* cited by examiner

MULTI-CORTICAL DENTAL IMPLANT ANCHOR, DENTAL IMPLANT KIT AND TEMPLATE

RELATED APPLICATIONS

This application is a National Phase Application of PCT Application No. PCT/IL2005/001046 having International Filing Date of Sep. 28, 2005, which claims priority from Israel Patent Application No. 164374, filed on Oct. 3, 2004, and Israel Patent Application No. 167421, filed on Mar. 14, 2005. The contents of the above Applications are all incorporated herein by reference.

1. Field of the Invention

The present invention relates to dental prosthesis in general and, in particular, to dental implants and anchoring devices and methods and kits therefor.

2. Background of the Invention

In cases requiring dental prosthesis, dental implants provide a support structure based in the jawbone for supporting the prosthesis. Most dental implants are generally cylindrical structures, which may be threaded, fitted into a vertical bore drilled into the jawbone. Before the prosthesis can be installed, the bone must heal from the drilling and harden around the implant, a process referred to as osseointegration. This is typically known to take a number of months during which any strain on or movement of the implant can inhibit or prevent successful osseointegration.

It is for this reason that additional support members or anchors have been employed to provide more secure and stable mounting of the implant and allow installation of the prosthesis or loading without the extensive waiting period. Another advantage of anchors is that they allow use of shorter implants, eliminating the need for supplementary bone graft surgery. Anchors may simply provide a broader base for the implant in the relatively soft and sponge-like, cancellous interior of the jawbone, or they may be based in the hard, cortical exterior thereof.

U.S. Pat. No. 6,450,812 to Laster et al. provides a detailed summary of these and other issues regarding dental implants and a review of representative prior art and is included herein by reference. The "Bi-cortical Dental Implant" disclosed therein requires additional, transverse drilling to accommodate the anchor, which further must fit into a conduit bored through the implant itself. This further requires specially fabricated or prepared implants. These factors complicate and lengthen the installation procedure, an obvious disadvantage for the patient, and further make the entire prosthesis more complicated and expensive.

SUMMARY OF THE INVENTION

The present invention seeks to provide a multi-cortical dental implant anchor and kit for installation of a dental implant, as well as a method therefor, that is simple to use, and provides almost instantaneous stabilization of the implant once installed, overcoming disadvantages of prior art.

There is thus provided, in accordance with a preferred embodiment of the present invention, an implant device implantable in a socket of a subject, comprising a dental implant having a generally elongate shank and a grippable region formed at a predetermined portion thereof, and an anchor including a first elongate member connected to a second elongate member connected by a bridge member; the first elongate member and the second elongate member having inner confronting surfaces spaced from each other and constructed to lockably engage the grippable region of the dental implant against movement with respect to the anchor.

a dental implant having a generally elongate shank and a grippable region formed at a predetermined portion thereof;

and an anchor including a first elongate member and a second elongate member connected by a bridge member, said first elongate member and said second elongate member having inner confronting surfaces spaced from each other and constructed to lockably engage said grippable region of said dental implant against movement with respect to said anchor, with said elongate members extending transversely across said elongate shank.

Preferably, the member having the longitudinal axis is a generally U-shaped member.

Still preferably, the first elongate member and the second elongate member each having first and second ends and adapted to simultaneously engage a tissue of a first cortical plate of the jawbone and optionally and preferably also a tissue of a second cortical plate of the jawbone, respectively, while lockably engaging the grippable region of the dental implant against pivoting in the direction transverse to the longitudinal axis, preferably against pivoting or moving in any direction.

Additionally in accordance with a preferred embodiment of the invention, the first and second elongate members are formed as prongs of a unitary anchor member, wherein the second ends of the prongs are free ends having a slightly narrowed configuration so as to easily enter bores formed in the cortical tissue.

Further in accordance with a preferred embodiment of the invention, the implant anchor is formed as a resilient compression member, and the distance between the prongs is less than the thickness of a predetermined exterior portion of the dental implant prior to engagement therebetween, and wherein the prongs are responsive to an elastic force applied thereacross so as to become separated from each other and thereby to facilitate insertion thereof about the implant, the elastic force subsequently serving to lockably engage the implant anchor with the dental implant.

Additionally in accordance with a preferred embodiment of the invention, the prongs have inward-facing portions which are adapted for gripping engagement with the predetermined exterior portion of the implant.

Further in accordance with a preferred embodiment of the invention, the exterior portion of the implant is formed as a narrowed waist portion.

Additionally in accordance with a preferred embodiment of the invention, the inward-facing portions of the prongs are curved, and the waist portion is configured to seat the curved inward-facing portions of the prongs.

Further in accordance with a preferred embodiment of the invention, the inward-facing portions of the prongs have a rectilinear form, and the waist portion is configured to seat the rectilinear inward-facing portions of the prongs.

Additionally in accordance with a preferred embodiment of the invention, the exterior portion of the implant has a screw thread formed thereon.

Further in accordance with a preferred embodiment of the invention, each of the inward-facing portions of the prongs has formed thereon one or more concave recesses, having formed thereon a screw thread adapted to screwably engage the screw thread formed on the exterior portion of the implant.

Additionally in accordance with a preferred embodiment of the invention, each of the inward-facing portions of the prongs terminates in a blade edge, adapted to lockingly engage the screw thread formed on the exterior portion of the implant.

Further in accordance with a preferred embodiment of the invention, the multi-cortical implant anchor also includes a generally outward-facing index member formed on the bridge member, adapted to determine the position of an implant positioning template having a recess configured for indexing engagement with the index member.

In accordance with a further embodiment of the invention, there is provided a multi-cortical self-locking dental implant kit, which includes a dental implant for placement in the jawbone of a subject, having a generally elongate shank; and a grippable region formed at a predetermined portion of the elongate shank, and a multi-cortical implant anchor, substantially as described above.

In accordance with yet a further embodiment of the invention, there is provided, preferably for use with the hereinabove-described implant and anchor, an implant positioning template having first and second interconnected mutually orthogonal template portions adapted for placement over the site of a dental implant, wherein the first template portion is an implant guide, and has formed therein at least one bore for guiding the angle of entry into the jawbone of a subject, of a tool employed for forming a bore into which the dental implant is to be placed, and wherein the second template portion is an implant anchor guide, and has formed therein at least two bores for guiding the angle of entry into a first cortical plate of the jawbone of a subject, of a tool employed for forming lateral bores through which the implant anchor is to be placed so as to interlock with the dental implant while simultaneously engaging a tissue of the first and second cortical plates of the jawbone.

Additionally in accordance with the present embodiment, the bridge member has formed thereon an outward-facing index member, and the second template portion has formed therein an indexing recess, the index member and the indexing recess being operative for mating engagement so as to position the at least one bore formed in the implant guide in a predetermined position relative to the implant anchor so that the implant anchor is located so as to receive the dental implant therein.

Further in accordance with the present embodiment, the implant positioning template includes apparatus for selectably adjusting the position of the first and second guide portions with respect to each other.

Additionally in accordance with the present embodiment, the kit also includes apparatus for adjusting the height of the implant positioning template with respect to the jawbone of the subject, at the site for the placement of the dental implant. This apparatus may take the forms, for example, of spacer apparatus adapted to be disposed between the first guide portion and the jawbone.

Preferably, the implant positioning template also includes a third guide portion, connected to the first guide portion and generally parallel to the second guide portion, wherein the second and third guide portions are adapted for seating about the jawbone at the site of the dental implant, so as to assist in the centering thereover of the at least one bore of the first guide portion.

There is also provided, in accordance with a further preferred embodiment of the invention, a method of anchoring a dental implant in the jawbone of a subject in a predetermined, substantially immovable position relative thereto, which includes:

a) anchoring in the first and optionally and preferably the second cortical plates of the jawbone of a subject, a multi-cortical implant anchor which has first and second elongate members interconnected by a bridge member; and b) inserting between the first and second elongate members a generally cylindrical dental implant having a generally elongate shank and a grippable region formed at a predetermined portion thereof, thereby to become interlocked with the implant anchor and anchored to the jawbone at two points in each of the first and second cortical plates thereof.

Additionally in accordance with the method of the invention, the step a) of anchoring includes the following steps:

c) forming a pair of anchor holes in the first cortical plate, at a selected position therein; and d) simultaneously inserting the first and second elongate members therethrough, so as to pass entirely through the first cortical plate, until the bridge member contacts the an outward-facing surface of the jawbone and free ends of the first and second elongate members pass through the second cortical plate, thereby to provide an anchor at four cortical anchor points, and the step b) of inserting a generally cylindrical implant includes the following steps:

e) forming an opening for the dental implant in the jawbone, at a selected position therein; and f) inserting the dental implant into the hole therefor, and wherein the steps of d) simultaneously inserting the first and second elongate members and e) inserting the dental implant combine to cause an interlocking between the dental implant and the multi-cortical anchor, so as to anchor the dental implant at the four cortical anchor points.

Further in accordance with the method of the invention, the generally cylindrical dental implant has a screw thread formed on its exterior, and the first and second elongate members of the implant anchor terminate in a narrowed inward-facing surface adapted to engage the screw thread, and wherein the step f) of inserting the dental implant into the hole therefor includes the step g) of screwing the generally cylindrical dental implant into the previously inserted implant anchor.

Additionally in accordance with the method of the invention, the generally cylindrical dental implant has a screw thread formed on its exterior, and wherein, subsequent to the step d) of simultaneously inserting the first and second elongate members, there is provided an additional step h) of forming screw threads in inward-facing portions of the first and second elongate members of the implant anchor, the screw thread portions being formed so as to have a position and orientation corresponding to a selected position and orientation at which the generally cylindrical dental implant is to be inserted;

and the step f) inserting the dental implant into the hole therefor includes the step i) of screwing the generally cylindrical dental implant for engagement with the screw thread portions formed in the implant anchor.

The method preferably also includes the following additional steps:

j) prior to the step c) of forming a pair of anchor holes, positioning over the site of a dental implant an implant positioning template having formed therein at least two anchor positioning holes, so as to assist in the selection of the position and orientation of the anchor holes; and k) removing the implant positioning template so as to permit the insertion of the first and second elongate members through the anchor holes so as to provide the anchor, wherein the step c) of forming a pair of anchor holes includes the step l) of inserting a hole forming tool through two of the anchor positioning holes of the implant positioning template, thereby to form the holes at the selected position and orientation.

Preferably, the method also includes after the step d) of simultaneously inserting the first and second elongate members, the step of m) positioning over the site of the dental implant an implant positioning template having formed therein at least one implant positioning hole, so as to assist in the selection of the position and orientation of the implant hole; and after the step e) of forming an opening for the dental implant, the step n) of removing the implant positioning template so as to permit the insertion of the dental implant, wherein the step e) of forming an opening for the dental implant includes the step o) of inserting a hole forming tool through a selected implant positioning hole of the implant positioning template, thereby to form the implant hole at the selected position and orientation.

Further in accordance with the method of the invention, the step p) of positioning an implant positioning template to assist in the selection of the position and orientation of the implant hole, includes the step q) of indexing the implant positioning template in relation to the implant anchor thereby to coordinate the position and orientation of the dental implant after the step of inserting the dental implant, with the position and orientation of the implant anchor.

According to yet another aspect of the invention there is provided a dental implant for use with a multi-cortical implant anchor as described hereinabove, the dental implant comprises a generally elongate shank and a grippable region formed at a predetermined portion of the shank, the grippable region being designed and constructed to be lockably engaged by the multi-cortical implant anchor, to thereby prevent pivoting of the dental implant in a direction other than rotation about its longitudinal axis. Preferably, the grippable region is threaded.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

Figure 1A:
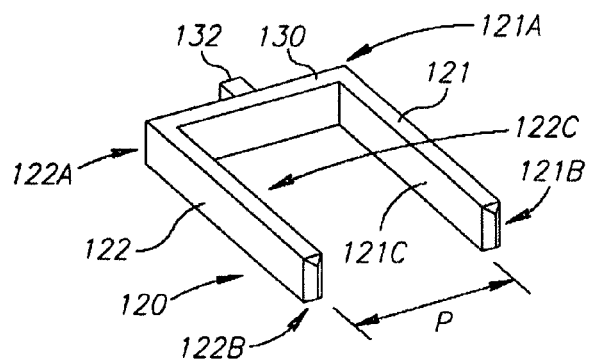
FIG. 1A is a schematic representation of a multi-cortical implant anchor, constructed in accordance with a preferred embodiment of the present invention.

The present invention is of dental implants and anchoring devices for dental implants, kits containing same, methods of using same and apparti for assisting in implementing the methods.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to FIGS. 1A, 1B, 1C, 2A, 2B, 3A, 3B, 4, 5A, 5B, 6A-6C, there is provided, in accordance with a preferred embodiment of the invention, a multi-cortical self-locking dental implant kit, which includes a dental implant, referenced generally 10, a multi-cortical implant anchor, referenced generally 20, and an implant positioning template, referenced generally 70. It will be noted that, with the exception of FIG. 1C, in all figures, the various components of the invention, as well as specific portions thereof which are described in conjunction with the drawings, similar reference numerals are employed to denote similar components and portions, but with the addition of a prefix to identify specific embodiments by the drawing in which they are shown. By way of example, therefore, implant 10 is denoted 110 in FIG. 1B, 310 in FIG. 3B, 510 in FIGS. 5A and 5B, and 610 in FIGS. 6B and 6C. Similarly, anchor 20 is denoted 120 in FIG. 1A, 220 in FIGS. 2A and 2B, 320 in FIGS. 3A and 3B, 420 in FIG. 4, 520 in FIG. 5B, 620 in FIGS. 6A, 6B and 6C.

Furthermore, when portions of the invention are being described in conjunction with more than a single embodiment, the basic reference numeral is used, without the addition of a prefix as mentioned above.

Figure 1B:
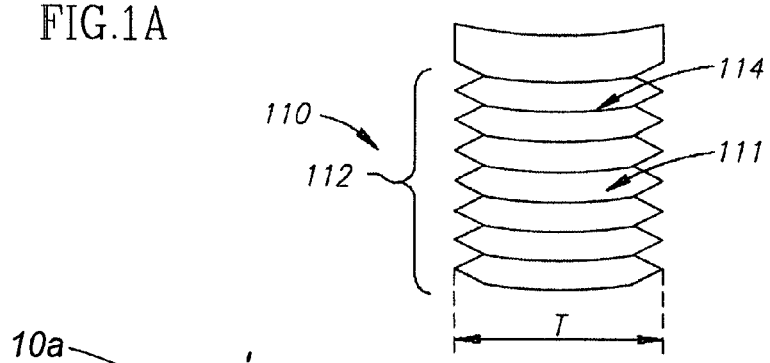
FIG. 1B is a schematic representation of a dental implant.
Figure 1C:
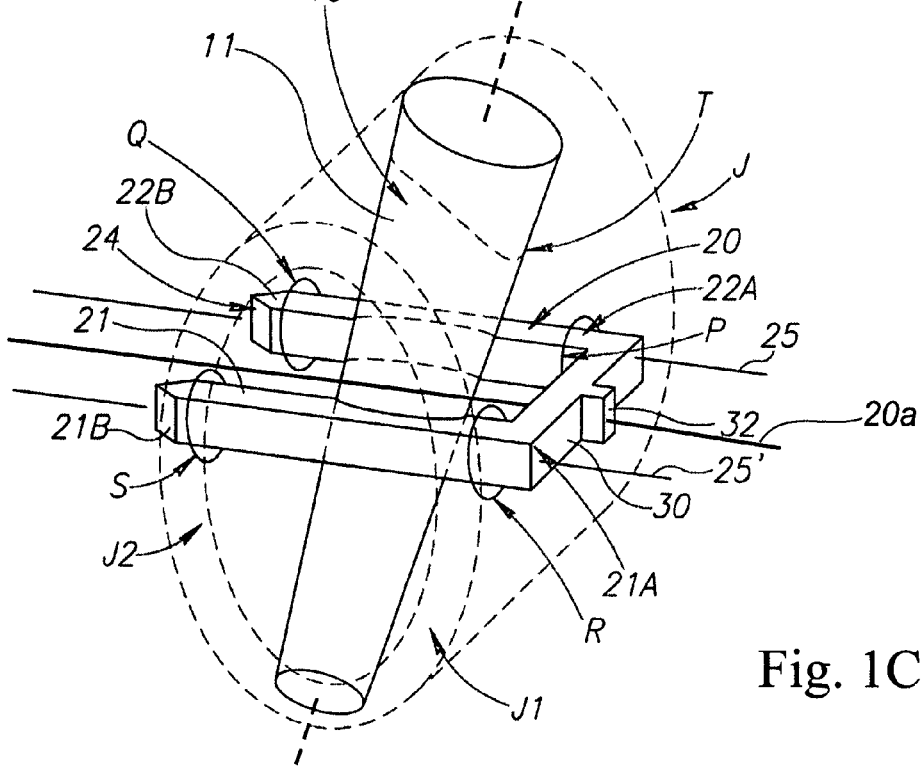
FIG. 1C is a schematic representation of a multi-cortically anchored self-locking implant in position within the jawbone of a subject, in accordance with a preferred embodiment of the present invention.

By way of further clarification, when referred to generally, such as in FIG. 1C, and without specific reference to a specific singularly illustrated embodiment, the implant and anchor are denoted simply by reference numerals 10 and 20, respectively, as above.

It will further be appreciated that even though the three main components of the invention, namely, implant 10, anchor 20 and template 70, together form an inventive multi-cortical kit, each of these components embodies inventive features in, and of itself. Accordingly, the description below of a multi-cortical self-locking dental implant kit, per se, and of a method of anchoring a dental implant, are not specifically intended to limit the invention to the kit only when taken as a whole, or to a method employing specifically that kit. Rather, the description of a kit and of use thereof is merely for convenience, and so as to illustrate a manner in which the inventive components of the present invention could best be used together, in accordance with a preferred embodiment of the present invention.

Referring now FIGS. 1A, 1B, 1C, 2A, 2B, 3A, 3B, 4, 5A, 5B, and 6A-6C, the present invention includes a dental implant 10 (FIGS. 1B, 3A, 3B, 3C, 3D, 5A, 5B, 5C, 5D, 6B and 6C) for placement in the jawbone of a subject, illustrated in outline at J in FIG. 1C. The illustrated implant 10 includes a generally elongate shank 11, and a grippable region 12 formed at a predetermined portion of the shank, so as to be gripped for interlocking engagement with implant anchor 20 (FIGS. 1A, 2B, 3C, 3D, 4, 5C, 5D, 6A, 6B and 6C). Implant anchor 10 is manufactured from any suitable surgical material, typically metal, such as titanium, zirconium, and tantalum. Implant anchor 10 has, as shown in FIG. 1C, a longitudinal axis 10a.

As shown, inter alia, in FIG. 1C, the multi-cortical implant anchor 20 of the present invention, is adapted for interlocking mating engagement with the dental implant 10 in a preselected position with respect to the jawbone J of a subject.

As exemplified in FIGS. 1A, 2B, 3C, 3D, 4, 5C, 5D, 6A, 6B and 6C, implant anchor 20 is preferably formed as a unitary member having the overall configuration of a U having a longitudinal axis 20a, and so as to have a first and second elongate members or prongs, referenced 21 and 22, respectively, and a bridge member thereacross, referenced 30 as described below in detail. Anchor 20 is designed such that, when applied to anchor the dental implant 10, the axes of the first and second elongate members 21 and 22 extend transversely across the longitudinal axis 20a of the implant.

Figure 2A:
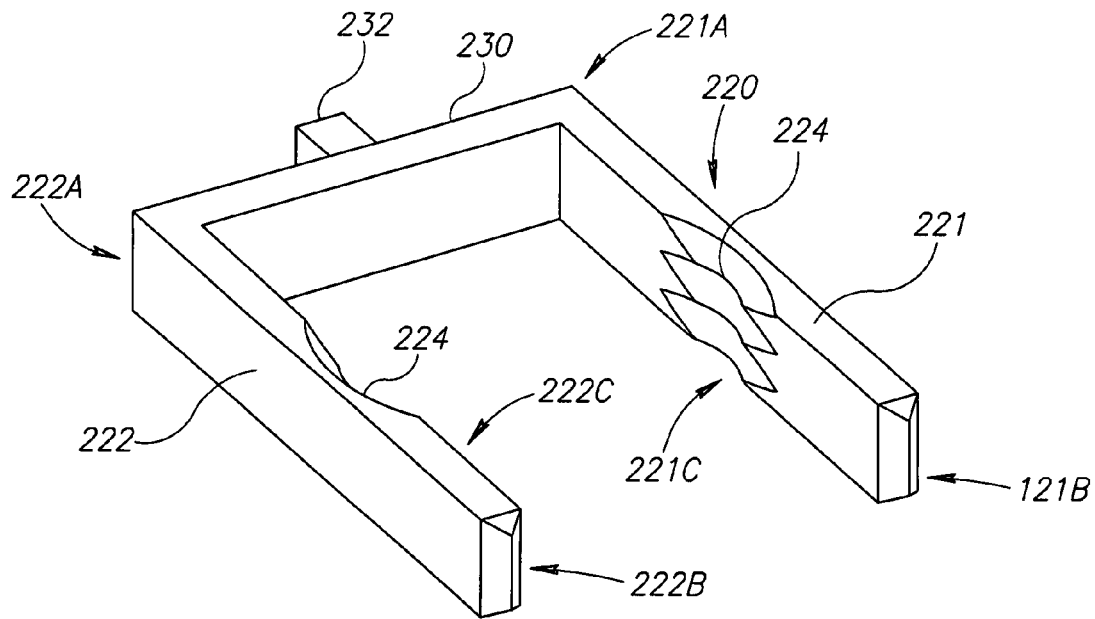
FIG. 2A is a schematic plan view of the anchor, during formation of a screw thread therein.
Figure 3A:
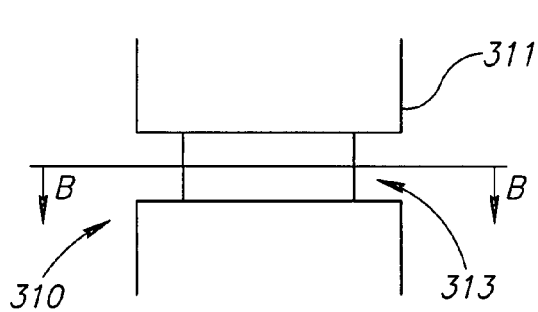
FIG. 3A is a schematic partial side view of an implant for use with a multi-cortical implant anchor as shown in FIG. 1A, and having a square waist portion in accordance with an alternative embodiment of the present invention.
Figure 3B:
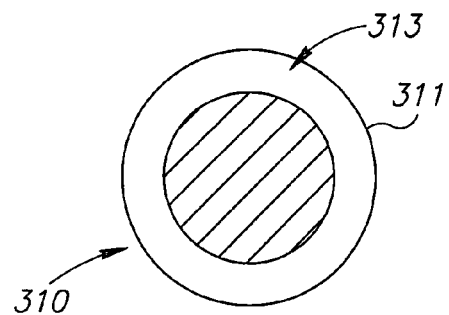
FIG. 3B is a is a cross-sectional view of the implant of FIG. 3B taken along line B-B therein, and multi-cortical implant anchor of FIG. 1A, after assembly thereof.
Figure 3C:
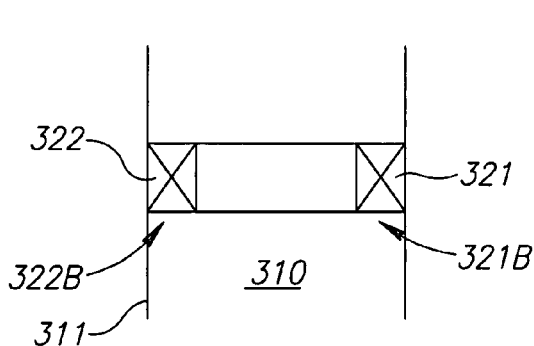
FIGS. 3C and 3D are views similar to those of FIGS. 3A and 3b, but showing the multi-cortical implant anchor after assembly thereof.
Figure 6A:
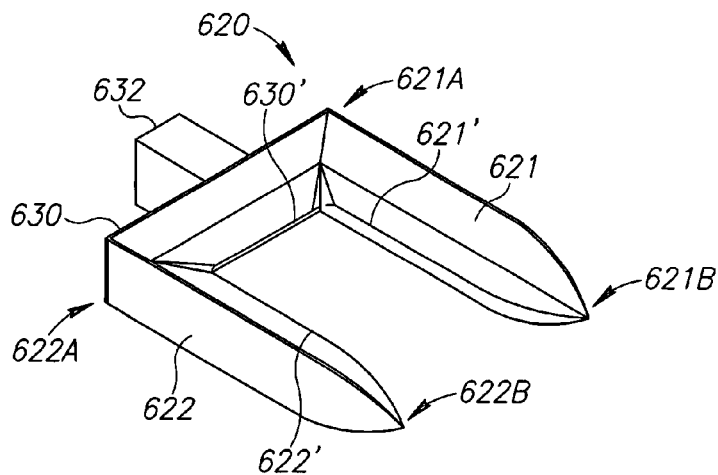
FIG. 6A is a schematic representation of a multi-cortical implant anchor for a dental implant, formed to engage a screw thread thereof, constructed in accordance with a further embodiment of the present invention.
Figure 6B:
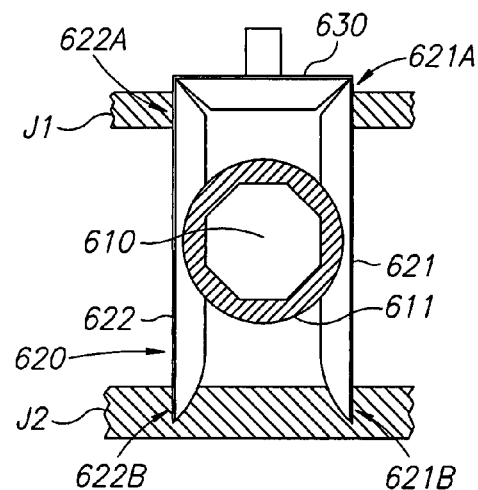
FIG. 6B is a schematic plan view of the multi-cortical implant anchor of FIG. 6A, after assembly thereof with an implant.

The first elongate member or prong 21 has first and second ends, respectively referenced 21a and 21b, and a longitudinal axis 25. The second elongate member or prong 22 is identical to the first elongate member 21, also having first and second ends, respectively referenced 22a and 22b, and a longitudinal axis 25'. Together, the elongate members 21 and 22 are operative to lockably engage the grippable region 12 of the dental implant 10, and further adapted, as illustrated in FIGS. 1C, 2A and 6B, to simultaneously engage a tissue of a first cortical plate J1 of the jawbone and a tissue of a second cortical plate J2 of the jawbone J, respectively, while interlocked with the dental implant, thereby to lock the dental implant at a first pair of cortical anchor points P, Q against pivoting in a direction transverse to the longitudinal axis of the first elongate member or prong 21 and preferably preventing any movement of the implant, such as quivering, of greater than 50-100 micrometers in any direction, other than, in some embodiments of the invention, a screw/rotation movement designed to bring the grippable region of the dental implant in contact with the first and second elongated members; and also to lock the dental implant at a second pair of cortical anchor points R, S against pivoting in a direction transverse to the longitudinal axis of the second elongate member or prong 22.

As described above, bridge member 30 is connected to or formed integrally with the first ends 21a and 22a of the first and second elongate members or prongs 21 and 22, and is adapted to contact the first cortical plate J1 of the jawbone J when, as illustrated in FIG. 1C, the multi-cortical implant anchor 20 is in a position of full locking engagement with the dental implant 10. The second ends 21b and 22b of the prongs or elongate members 21 and 22 are free ends which, as illustrated in FIGS. 1A, 1C, 2A, 2B, 3C, 4, 5C, 6A and 6B, have a slightly narrowed or sharpened configuration so as to easily enter bores formed in the cortical tissue upon placement of the anchor therein. This will be more fully understood from the method descriptions, hereinbelow.

In accordance with a preferred embodiment of the invention, and as exemplified, inter alia, in FIGS. 1A and 1B, the implant anchor 10 is formed as a resilient compression member, and the distance P between the prongs is less than the thickness T of the predetermined portion of the dental implant prior to interlocking mating engagement therebetween.

In accordance with an embodiment of the invention in which the implant 10 is positioned between the cortical plates J1 and J2, and only afterwards is the implant anchor 20 inserted for engagement therewith, a mating force may be applied in order to effect the required mating engagement between the implant and the anchor. In response to such a mating force, the prongs 21 and 22 are responsive to become further separated from each other, such that the distance therebetween increases to T, thereby to facilitate insertion thereof about the implant. This mating or elastic force subsequently serves to lock the inward-facing portions 21c and 22c of the prongs 21 and 22 in gripping engagement with the implant 10, so as to result in the multi-cortical anchoring illustrated in FIG. 1C.

Figure 2B:
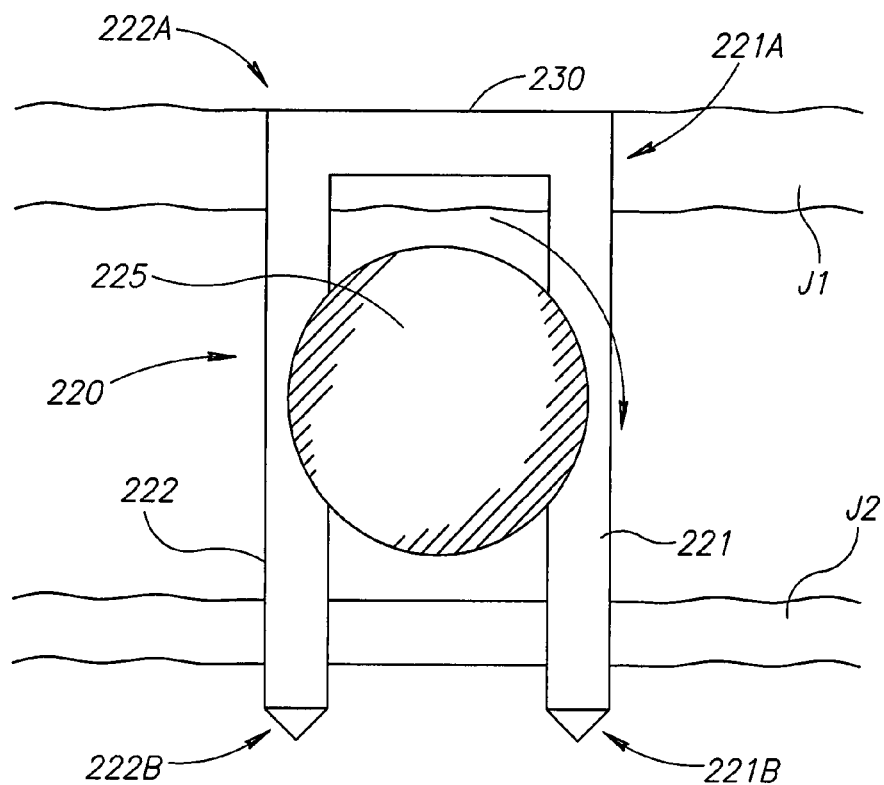
FIG. 2B is a schematic representation of the anchor of FIG. 1A, after formation of a screw thread therein.

Referring now once more to FIGS. 1A, 1C, and 2B, it is seen that, in accordance with a preferred embodiment of the invention, a generally outwardly protruding index member 32 is provided on bridge member 30. As will be appreciated more fully from a description of a method of the invention below, the purpose of index member 32 is, together with a corresponding indexing recess 34 (FIGS. 7A, 7B and 7D) formed within an implant positioning template 70, to determine the position of the template 70 and thus of the implant 10 and implant anchor 20.

Referring now to FIGS. 7A-7D, there is shown, in varying embodiments, implant positioning template 70, for assisting in the exact positioning of both implant 10 and implant anchor 20, as shown and described above in conjunction with FIGS. 1A, 1C, 2A, and 2B. In the four drawings FIGS. 7A-7D there are shown implant positioning templates constructed in accordance with different embodiments of the invention. Accordingly, similar components in the different embodiments are denoted with similar reference numerals, but with the addition of a suffix corresponding to the specific drawing. By way of example, the template 70 is shown as 70a in FIGS. 7A, 70b in FIG. 7B, and so on.

Figure 7A:
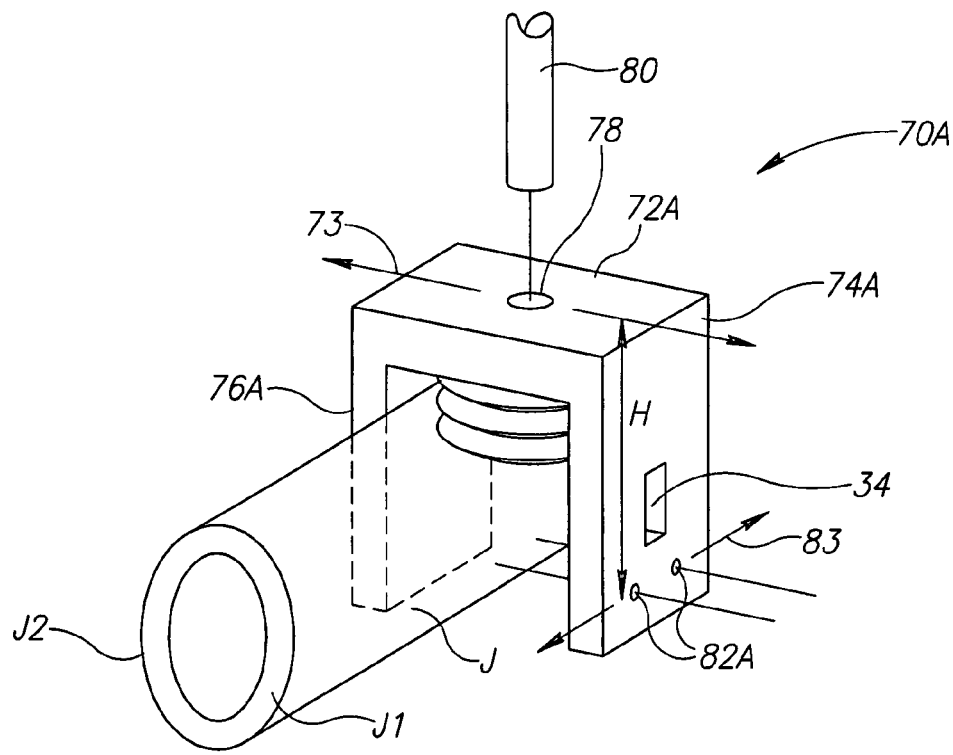
FIGS. 7A, 7B, 7C and 7D are schematic views of an implant positioning template, constructed and operative in accordance with various embodiments of the present invention.

The function of template 70 is to assist in the precise positioning of the implant anchor 20, and thus of the implant 10, in the jaw J (FIGS. 1C and 7A). To this end, template 70 is provided with first second and third interconnected, mutually orthogonal template portions, respectively referenced 72, 74 and 76, adapted for placement over the site of a dental implant.

As seen by the schematic representation in FIG. 7A, the first template portion 72 is an implant guide, and has formed therein at least one bore 78 for guiding the angle of entry into the jawbone of a subject, of a tool 80 employed for forming in the jawbone a bore into which the dental implant is to be placed. The second template portion 74 is an implant anchor guide, and has formed therein at least two bores 82 for guiding the angle of entry into a first cortical plate J1 of the jawbone of a subject, of a tool employed for forming lateral bores through which the implant anchor 20 is to be placed, ultimately being in simultaneous mutual interlocking engagement with the dental implant 10 and tissue of the first and second cortical plates J1 and J2 of the jawbone. The third guide portion 76 is seen to be connected to the first guide portion 72 so as to have a generally parallel orientation relative to the second guide portion 74, and is operative, together with the second guide portion 74, to center bore 78 over the jawbone Template 70 may be used for placement of the implant 10 and thereafter the implant anchor 20, such as required, for example, for the positioning of the implants shown and described hereinbelow in conjunction with the embodiments of FIGS. 3A-5D, wherein the implant 10 is first positioned and only subsequently is the anchor 20 is inserted. Template 70 is used to the greatest advantage, however, in conjunction with the embodiments of FIGS. 1A-2B, in which the anchor 20 is first positioned, and subsequently acts as a guide for placement of the implant 10.

In accordance with this latter use, formed in second template portion 74 is indexing recess 34. It will be appreciated that once the implant anchor 20 has been properly positioned, the template 70 may be positioned over the implant site into a position which is indexed by virtue of the mating engagement between the index member 32 (FIGS. 1A, 1C and 2B), and the indexing recess 34. This permits the forming of a hole in the jaw for the implant, in precise relation to the position an orientation of the anchor 20 within the jawbone.

In view of the fact that the precise positioning of the bores for both the implant 10 and the implant anchor 20 will normally be determined at the time of placement, it is preferred that the relative positioning of the bores 78 and 82 formed in the first and second template portions 72 and 74, respectively, be adjustable. This is indicated schematically by arrows 73 and 83.

Figure 7B:
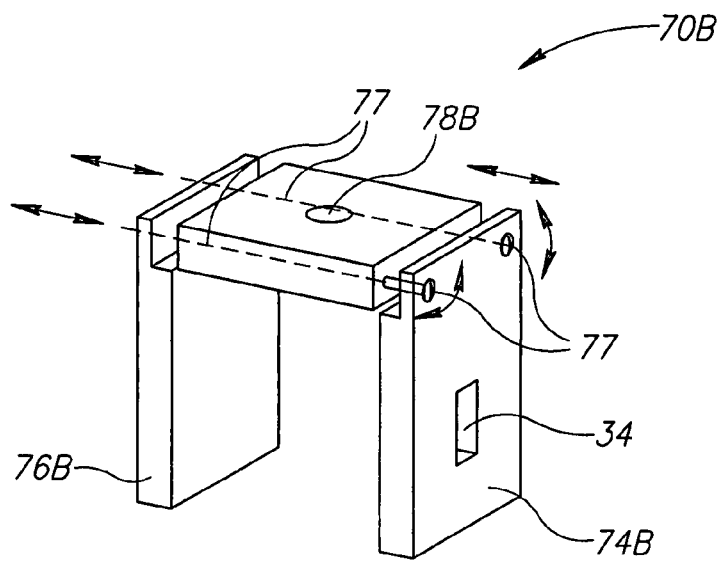
Figure 7C:
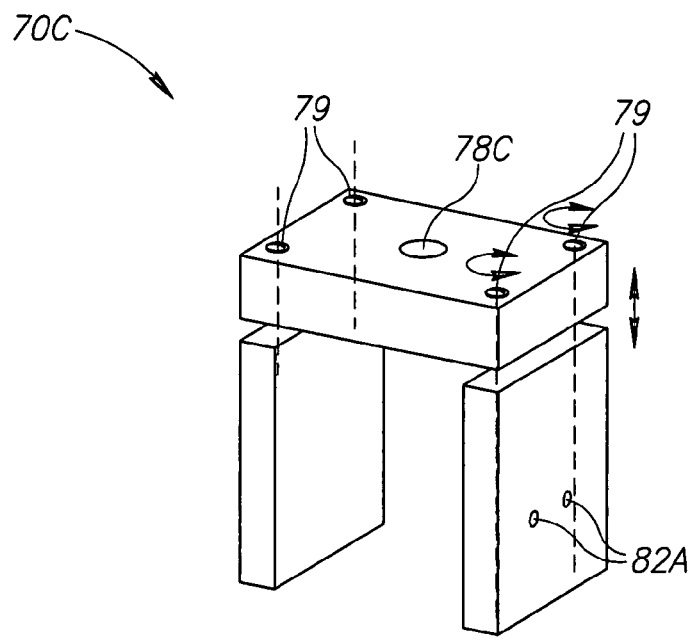
Figure 7D:
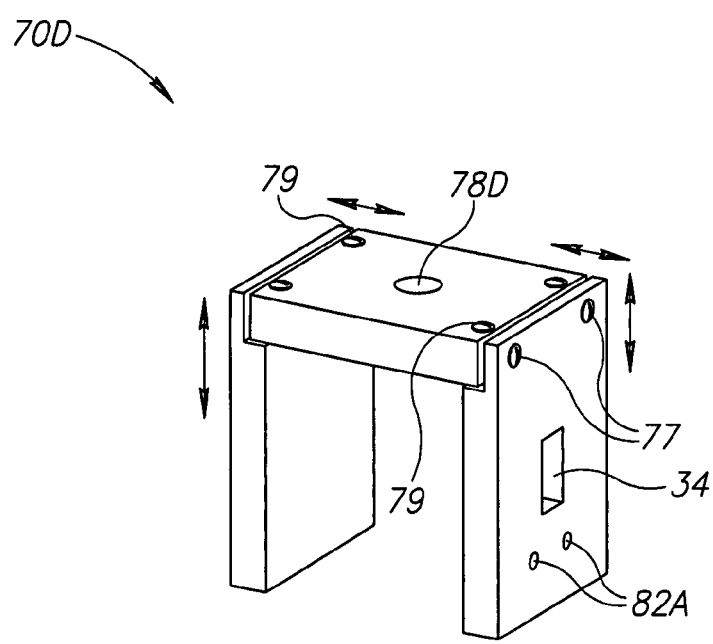

Accordingly, and in accordance with further preferred embodiments of the invention, in each of FIGS. 7B, 7C and 7D, there is illustrated a slightly different exemplary modification of the template 70 of the present invention.

Briefly, in FIG. 7B, it is seen that the second and third guide portions 74b and 76b are laterally adjustable with respect to each other and to the intervening first guide portion 72b, as by way of a plurality of horizontal screw members, denoted by reference numerals 77. It will be appreciated that screw members 77 may be adjusted in order to increase or decrease the lateral pacing between the second and third guide portions 74b and 76b, thereby adjusting the position first guide portion 72b, and consequently, implant positioning bore 78b.

In the embodiment of FIG. 7C, it is seen that, as opposed to the embodiment of FIG. 7B, in which the second and third guide portions 74b and 76b are laterally adjustable, they are adjustable only with respect to the first guide portion 72c, as by way of vertical screw members 79. Clearly, this is useful when seeking to adjust the vertical positioning of the holes to be framed for the anchor 20 (not shown).

Most useful, is the embodiment of FIG. 7D, which incorporates the improvements of both of the embodiments FIGS. 7B and 7C, and which does thus not require further description.

Referring now to FIGS. 1C-2B, there is described a method of anchoring a dental implant 10 in the jawbone J of a subject in a predetermined, substantially immovable position relative thereto. By way of clarification, the reference numerals employed hereinbelow are those of FIG. 1C, although they are also relate to similar portions and components in FIGS. 2A and 2B, as appropriate.

Accordingly, the method thus includes the following steps:

1. Position template 70 over a selected implant site.
2. Form lateral holes in the cortical plate J1 of the jawbone, via anchor positioning holes 82a of template 70.
3. Remove template 70.
4. Carefully insert the prongs or elongate members 21 and 22 of the implant anchor through the lateral holes, until the ends 21b and 22b of the elongate members 21 and 22 become firmly embedded in the second cortical plate J2, and so that the index member 32 protrudes outwardly from the first cortical plate J1.
5. Position template 70 over the implant site, so that the index member 32 enters the indexing recess 34, therefore determining the position of the implant positioning bore 78 with respect to the position of the anchor 20.
6. Insert through positioning bore 78 tool 80 employed for forming in the jawbone a bore into which the dental implant 10 is to be placed, in precise position and orientation with respect to the anchor 20.
7. Removing the tool 80 and optionally, inserting an alternative, thread forming tool (not shown) through positioning bore 78, and forming a screw thread, of the exact size, angle and position, required; and completing the formation of the bore in the jawbone, for the implant.
8. Removing template 70, and inserting implant 10 into the bore formed in the jawbone, by a screwing action, thereby to lockably secure the implant in position, at multiple points in the cortex.
9. Trimming off any externally protruding portions of the anchor 20, including the index member 32 and ends 21b and 22b of the anchor prongs 21 and 22.

Referring now to FIGS. 3A-5D, in accordance with one embodiment of the invention, the exterior of the implant 10 is formed as a narrowed waist portion or peripheral groove.

Figure 3D:
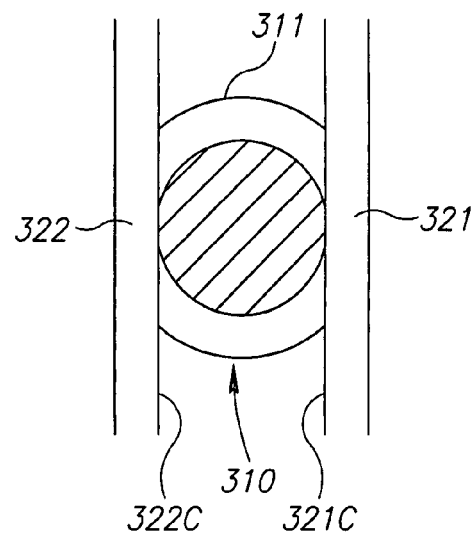

In accordance with one embodiment of the invention, the groove, referenced 313 is of generally rectilinear shape, as seen in FIGS. 3A-3D, and is adapted to seat the rectilinear shaped inward-facing prongs 321 and 322 of an appropriately formed implant anchor 320, as shown in FIG. 3D. As will be understood with reference to FIGS. 3B and 3D, the fact that the groove is uniform along the entire circumference of the implant 310, means that regardless of the angle of axial rotation of the implant, it will always be possible to insert the anchor 320 into the groove 313 so as to become matingly engaged therewith as described, provided that the implant 310 and anchor 320 are in mutual positional and angular registration.

Figure 4:
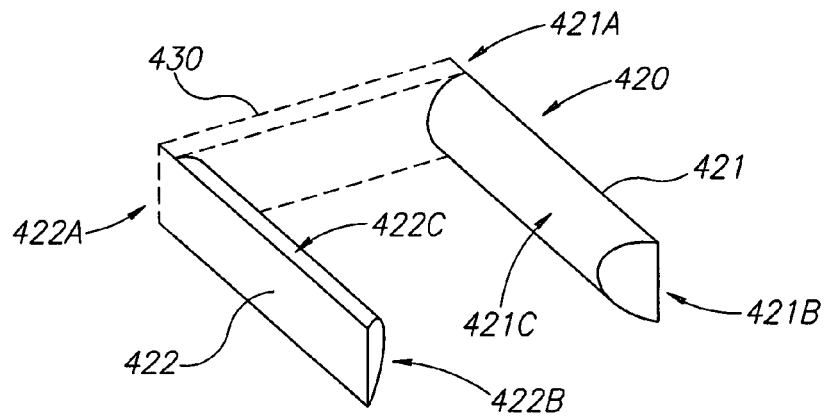
FIG. 4 is a schematic representation of a multi-cortical implant anchor, constructed in accordance with yet a further embodiment of the present invention.
Figure 5A:
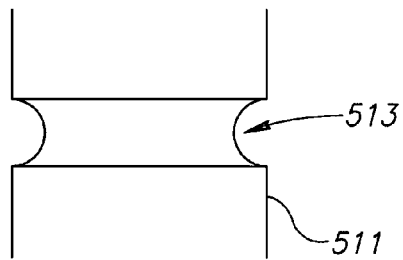
FIGS. 5A and 5B are side and sectioned views of an implant for use with the multi-cortical implant anchor of FIG. 4, and having a rounded waist portion in accordance with an additional embodiment of the present invention.
Figure 5B:
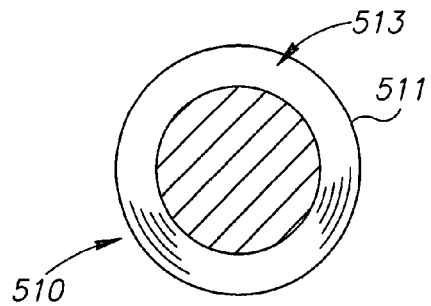
Figure 5C:
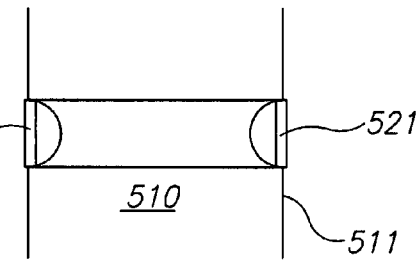
FIGS. 5C and 5D are corresponding views of the implant of FIGS. 5A and 5B with the multi-cortical implant anchor of FIG. 4, after assembly thereof.
Figure 5D:
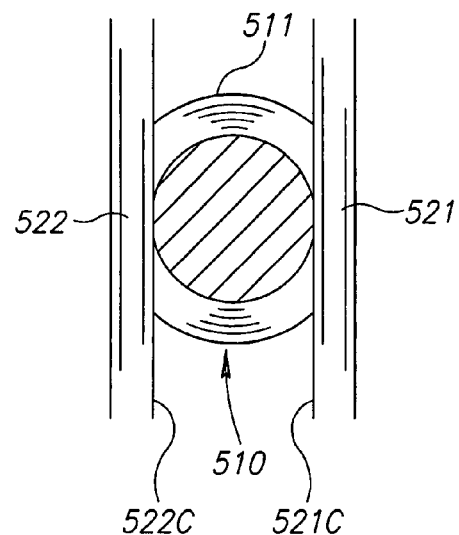

A similar advantage accrues from the embodiment illustrated in FIGS. 4-5D. As seen in FIGS. 4, 5C and 5D, the inward-facing portions 21c and 22c of the respective prongs 21 and 22 may be curved, and the waist portion or groove 513 of the implant 510 is formed as a circumferential groove having a generally semi-circular or—elliptical cross-section, so as to seat the curved inward-facing portions of the prongs as illustrated in FIG. 5C.

Referring now to FIGS. 1A, 1B, 2A, 2B, and 6A-6C, in accordance with a preferred embodiment of the invention, there is employed an implant 10 of which the exterior, grippable portion 12 has a screw thread 14 formed thereon. This has a particular advantage, as will be described below, in that when in use, the anchor 20 may be positioned first in a multi-cortical anchoring position as illustrated in FIG. 1C, after which the implant 10 may be inserted with a screwing action, into precisely the correct position and orientation.

Referring now specifically to FIGS. 2B, this precision screwing insertion may be achieved by forming in a concave recess formed on each of the inward-facing portions of the prongs, a screw thread 24 configured to screwably engage the screw thread 14 of the implant 10. While, in accordance with one embodiment of the invention, the anchor screw threads 24 may be formed at the time of manufacturing the implant anchor, this would inevitably necessitate the stocking of a number of different anchors, corresponding to the precise positioning of the implant that may be required.

Accordingly, in accordance with a preferred embodiment of the invention, and as seen in FIG. 2A and as will be further described hereinbelow in conjunction with a method of the invention, the screw thread is not formed at the time of manufacture, but is manufactured as a 'blank', substantially as per the anchor 120 illustrated in FIG. 1A.

Figure 6C:
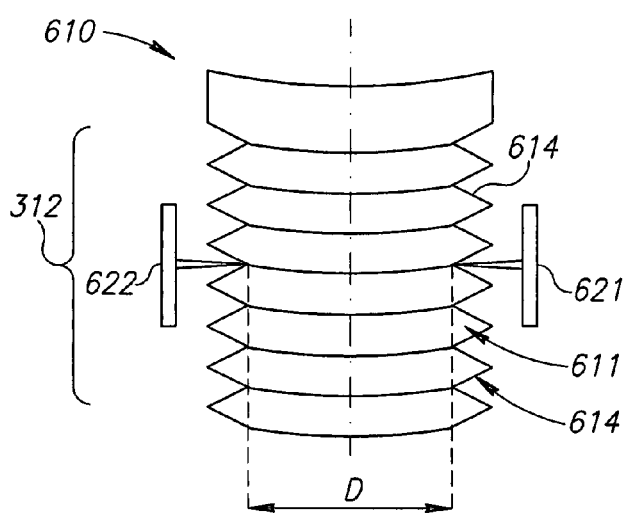
FIG. 6C is a schematic side view of the implant and multi-cortical implant anchor after assembly, as seen in FIG. 6B.

In use, therefore, and as illustrated in FIG. 2A, the anchor 220 is inserted into position within the jawbone of a subject, so as to be properly anchored in the first and second cortical plates J1 and J2. After insertion, it is then possible to determine the precise position and angle at which the implant is to be inserted, preferably by use of the template 70 as shown and described in conjunction with FIGS. 7A-7D. Subsequently, as illustrated schematically in FIG. 2A, and after the formation of a required opening into which the implant 10 is to be introduced, a thread-forming tool 225 is introduced into the opening so as to form screw threads 224 on the inward-facing portions of the prongs 221 and 222, at precisely the correct position and angle at which the implant 10 is to be placed. Finally, the implant may be screwed into position into the newly formed screw threads 224 in the anchor. Referring now to FIGS. 6A-6C, in accordance with an alternative embodiment of the invention, there is provided an anchor 620 for use with a dental implant 610, constructed and operative in accordance with an embodiment of the present invention. Implant anchor 620 is generally U-shaped, with two generally parallel prongs 621 and 622 integrally formed with and connected to each other generally orthogonally by bridge 630. Prongs 621 and 622 are of a predetermined length and have tapered or sharpened ends 150. Bridge 630 and prongs 621 and 622 of implant anchor 620 all have blades, 630', 621' and 622' respectively, protruding internally relative to the U-shape of implant anchor 620, and generally orthogonally thereto. Implant anchor 620 is typically fabricated of titanium, but may also be fabricated of zirconium, tantalum, or any other biocompatible material that is suitably strong and resilient.

Implant anchor 620 is employed to anchor dental implant after installation thereof in a bore drilled or otherwise suitably formed in a jawbone of a dental patient. Referring now to FIG. 6B, implant anchor 620 is seen to anchor dental implant 610 installed in a jawbone shown schematically by the first and second cortical plates, J1 and J2. As shown in the drawing, implant anchor 620 has been inserted through external cortical plate J1 until bridge 630 abuts the outer cortical surface and blade 630' of bridge 630 is embedded therein.

It should be noted that, in some cases, implant anchor 620 may be advantageously installed in the jawbone of the patient prior to installation of dental implant 610, and the dental implant 610 would be screwed into a bore located between prongs 621 and 622 of implant anchor 620 until it is lockingly engaged therewith at the desired position. One advantage is that implant anchor 620, once installed in the jawbone of the patient, serves as a guide for the placement of dental implant 610 in the desired location. In such cases the threaded portion of dental implant 610 may be tapered rather than cylindrical in shape, so that the proper position or depth determines the diameter of the dental implant where it interlocks with implant anchor 620.

Implant anchor 620 is designed and fabricated with prongs 621 and 622 thereof of a length such that, when implant anchor 620 is fully inserted in the jawbone, as described hereinabove, the tapered or sharpened ends 621b and 622b thereof are embedded in the tissue of the second, in this case internal, cortical plate J1 of the jawbone without emerging therefrom, as shown in the drawing. In a case where ends 621b and 622b do emerge and protrude slightly from internal cortical plate J1 of the jawbone, the ends 621b and 622b can be cut or otherwise shortened. Further, implant anchor 620 is designed and fabricated with bridge 630 thereof of a length so that the distance between blades 621' and 622' thereof is slightly less than the diameter of dental implant 610 where they engage and interlock therewith.

It should be noted that implant anchor 620 may be installed either from the internal cortical plate J1 to the external cortical plate J2, or the external cortical plate J2 to the internal cortical plate J1 of the jawbone of the patient, as may be determined by the dental practitioner.

Referring briefly now to FIG. 6C, it is seen that each of prongs 621 and 622 of the implant anchor 620 has a tee-shaped cross-section configuration, oriented such that the flat top of the tee is generally parallel to the axis of the implant 616, and the blades 621' and 622' of each prong forms the central leg of the tee. Blades 621' and 622' of prongs 621 and 622 engage the troughs of the thread 614 of dental implant 610, wherein the trough-to-trough diameter D of dental implant 610 is slightly greater than the spacing between the inner edges of blades 621' and 622' of prongs 621 and 622 of the implant anchor. This difference between D and the spacing will ensure that blades 621' and 622' of prongs 621 and 622 of the implant anchor exert a compression force on dental implant 610, providing an interlocking engagement therewith.

Upon insertion of implant anchor 620 into the jawbone around dental implant 610 installed therein, prongs 621 and 622 thereof are displaced in an outward direction. Since blades 621' and 622' of prongs 621 and 622 are smoothly and gradually tapered toward ends 621b and 622b thereof, this displacement will be gradual. Since implant anchor 620 has blade 630' of bridge 630 thereof embedded in the external cortical plate J2 of the jawbone and the ends 621b and 622b of both prongs 621 and 622 thereof embedded in the internal cortical plate J1 of the jawbone, dental implant 610 is effectively anchored immovably with respect to the hard cortical plates J2 and J1 of the jawbone by implant anchor 620. This secure and stable anchoring can allow a prosthesis to be installed on dental implant 610 and loaded without an extensive waiting period. It also allows use of shorter implants, eliminating the need for supplementary bone graft surgery.

As will be understood by those skilled in the art, the smoothly and gradually tapered profile of ends 621b and 622b of blades 621' and 622' of prongs 621 and 622 allows for a small amount of "play" in the alignment of implant anchor 620 with respect to dental implant 610 as it is being installed, since the taper of ends 621b and 622b guide blades 621' and 622' of prongs 621 and 622 around dental implant 610 as they engage during installation.

It should also be noted, as with the embodiments of FIGS. 1A-2B, that implant anchor 620 may be installed prior to the installation of dental implant 610, so as to serve as a guide to placement of dental implant 610 at the desired location in the jawbone of the patient. In such cases, dental implant 610 is screwed into the space between prongs 621 and 622 of implant anchor 620, which is fixed by virtue of being embedded at multiple points in the cortical tissue of the jawbone of the patient, as described hereinabove. Dental implant 610 is screwed into place; its threads engaging blades 621' and 622' of prongs 621 and 622 of implant anchor 620, until dental implant 610 is at the desired height or vertical position with respect to the jawbone of the patient and interlocking engagement with implant anchor 620 is achieved. Choice of a dental implant 610 with a threaded portion that is slightly tapered, can further serve to determine this optimal vertical positioning.

In accordance with a preferred embodiment of the present invention, the present invention further includes, for a patient requiring a dental prosthesis, a method employing a multi-cortical implant anchor as described hereinabove, for anchoring a dental implant in the jaw of the patient, including the following steps:

selecting a suitable dental implant 610 for a prosthesis required by a patient;

providing a suitable U-shaped implant anchor 620, as described hereinabove and as shown in FIG. 6A, to anchor the dental implant 610 in the jawbone J (FIG. 1C) of the patient;

installing the dental implant 610 in the jawbone J (FIG. 1C) of the patient;

aligning the implant anchor 620 so the prongs 621 and 622 of the U are on either side of the installed dental implant 610, as shown in FIG. 6C, at a suitable point along axis thereof along the jawbone J (FIG. 1C) of the patient;

inserting the implant anchor 620 through a first cortical plate of the jawbone J (FIG. 1C) of the patient until the implant anchor 620 engages the dental implant 610; and continuing to insert the implant anchor 620 until the blades 621' and 622' of the prongs 621 and 622 of the implant anchor 620 are in interlocking engagement with the dental implant 610.

Further, the step of providing a suitable U-shaped implant anchor 620 includes the sub-steps of:

selecting a U-shaped implant anchor 620 having a bridge 630 of a length smaller by a predetermined amount than the diameter of the dental implant 610; and selecting a U-shaped implant anchor 620 having prongs 621 and 622 of lengths so that the ends thereof will be embedded in, without protruding from, a second cortical plate of the jawbone J (FIG. 1C) of the patient when the implant anchor 620 is fully inserted into the jawbone J (FIG. 1C) of the patient at the location requiring the prosthesis, and wherein the step of continuing to insert is further continuing to insert the implant anchor 620 until the blade 630' of the bridge 630 engages the first cortical plate of the jawbone J (FIG. 1C) of the patient and until the tapered or sharpened end portions of the prongs 621 and 622 of the U of the implant anchor 620 are embedded in the second cortical plate of jawbone J (FIG. 1C), as shown in FIG. 6B.

It should be noted that, while in the present embodiment, the implant anchor 620 is installed from the external cortical plate to the internal cortical plate of the jawbone J (FIG. 1C) of the patient, there are cases, as is known to those familiar with the art, where an implant anchor 620 may be advantageously installed from the internal cortical plate to the external cortical plate; and these cases are also included in the present invention. Thus the first and second cortical plates of the embodiments discussed hereinabove may also refer to internal and external cortical plates, respectively. These cases and embodiments are also included in the present invention.

In accordance with a further preferred embodiment of the present invention, the present invention further includes, for a patient requiring a dental prosthesis, a method employing a multi-cortical implant anchor 620 as described hereinabove, for placement of a dental implant 610 in the jaw of the patient, in which the implant anchor 620 is installed in the jaw of the patient prior to installation of the dental implant 610 therein. In this embodiment, the implant anchor 620 further serves as a guide for the placement of the dental implant 610 at the desired location in the jaw of the patient. The method of the present embodiment includes the following steps:

selecting a suitable threaded dental implant 610, which may further be tapered, for a prosthesis required by a patient;

providing a suitable U-shaped implant anchor 620, as described hereinabove and as shown in FIG. 6A, to guide the placement of and to anchor the dental implant 610 in the jawbone J (FIG. 1C) of the patient;

aligning the implant anchor 620 so that the prongs 621 and 622 thereof are on either side of the desired location for installing the dental implant 610 for the required prosthesis, at a predetermined point along the axis of the dental implant 610 where it is to be installed in the jawbone J (FIG. 1C) of the patient; inserting the implant anchor 620 through a first cortical plate of the jawbone J (FIG. 1C) of the patient;

continuing to insert the implant anchor 620 until the blade 630' of the bridge 630 engages the first cortical plate of the jawbone J (FIG. 1C) of the patient and until the tapered or sharpened end portions of the prongs 621 and 622 of the U of the implant anchor 620 are embedded in a second cortical plate of jawbone J (FIG. 1C); and installing the dental implant 610 in the jawbone J (FIG. 1C) of the patient so that the blades 621' and 622' of the prongs 621 and 622 of the implant anchor 620 are in interlocking engagement with the thread 614 of the dental implant 610, as shown in FIG. 6C.

Further, the step of providing a suitable U-shaped implant anchor 620 includes the sub-steps of:

selecting a U-shaped implant anchor 620 having a bridge 630 of a length smaller by a predetermined amount than the diameter D of the dental implant 610 at the predetermined point along the axis thereof; and selecting a U-shaped implant anchor 620 having prongs 621 and 622 of lengths so that the ends thereof 621b and 622b will be embedded in the second cortical plate J2 of the jawbone J (FIG. 1C) of the patient when the implant anchor 620 is fully inserted into the jawbone J (FIG. 1C) of the patient, at the location requiring the prosthesis, as shown in FIG. 6B.

Further in accordance with the method of the present embodiment of the invention, the step of installing the dental implant 610 includes screwing the dental implant 610 into the jawbone J (FIG. 1C) of the patient until the blades 621' and 622' of the prongs 621 and 622 of the implant anchor 620 are in interlocking engagement with the thread 614 of the dental implant 610 at the predetermined point along the axis thereof.

Additionally, the method includes, before the step of aligning the implant anchor 620, the step of forming a bore in the jawbone J (FIG. 1C) of the patient at a predetermined location for installing the dental implant 610 therein, and wherein the step of aligning the implant anchor 620 further includes aligning the implant anchor 620 so that the prongs 621 and 622 thereof are on either side of the bore.

Alternatively, the method includes, before the step of installing the dental implant 610, the method includes the step of forming a bore in the jawbone J (FIG. 1C) of the patient at a predetermined location for installing the dental implant 610 therein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An implant device, comprising:
   a dental implant having a generally elongate shank and a grippable region formed at a predetermined portion thereof; and
   an anchor including a first elongate member and a second elongate member connected by a bridge member,
   said first elongate member and said second elongate member having inner confronting surfaces spaced from each other and constructed to lockably engage said grippable region of said dental implant against movement with respect to said anchor, with said elongate members extending transversely across said elongate shank, said elongate members being insertable into respective holes made laterally through the cortical jawbone and into a rear of the jawbone of a patient such that a portion of the confronting surfaces of the anchor is within a cavity in the jawbone while the bridge member of the anchor connecting the confronting surfaces remains outside the jaw bone, and wherein a coronal end portion of the dental implant is in a position which enables mounting a prosthesis thereon.

2. The implant device of claim 1, wherein said anchor is of a generally U-shaped configuration.

3. The implant device of claim 1, wherein each of said first elongate member and said second elongate member has first and second ends dimensioned to simultaneously engage a tissue of a first cortical plate of the jawbone and a tissue of a second cortical plate of the jawbone, respectively, while lockably engaging said grippable region of said dental implant against movement with respect to said anchor.

4. The implant device of claim 3, wherein said first and second elongate members are formed as prongs of said anchor, and wherein free ends of said prongs have a narrowed configuration so as to easily enter bores formed in the cortical tissue.

5. The implant device of claim 4, wherein said anchor is of elastic material, and the distance between said prongs is less than the thickness of said predetermined portion of the dental implant prior to engagement therebetween, said prongs becoming separated from each other upon the insertion of said dental implant to lockably engage said dental implant.

6. The implant device of claim 1, wherein said grippable region of said implant is formed as a narrowed waist portion.

7. The implant device of claim 6, wherein said confronting surfaces of said elongate members include curved portions, and said waist portion of the implant is configured to seat in said curved portions in the confronting surfaces of said elongate members.

8. The implant device of claim 1, wherein said confronting surfaces of said elongate members have a stepped construction, and a narrowed waist portion of the implant is configured to seat in said stepped construction of said elongate members.

9. The implant device of claim 1, wherein said grippable region of said dental implant has a screw thread formed thereon.

10. The implant device of claim 9, wherein each of said elongate members has formed thereon at least one screw thread adapted to screwably engage a screw thread formed on said grippable region of said dental implant.

11. The implant device of claim 9, wherein each of said confronting surfaces of said elongate members terminates in a blade edge adapted to lockably engage said screw thread formed on said grippable region of said dental implant.

12. The implant device of claim 1, wherein said anchor also includes a generally outward-facing index member formed on said bridge member, adapted to determine the position of an implant positioning template having a recess configured for indexing engagement with said index member.

13. A device according to claim 1, said anchor being designed such that, when applied to anchor the dental implant, the bridge member is external of said socket.

14. A multi-cortical self-locking dental implant kit comprising an implant device according to claim 1, and an implant positioning template having first and second interconnected mutually orthogonal template portions adapted for placement over the site of a dental implant,
   wherein said first template portion is an implant guide, and has formed therein at least one bore for guiding the angle of entry into the jawbone of a subject, of a tool employed for forming a bore into which said dental implant is to be placed,
   and further wherein said second template portion is an implant anchor guide, and has formed therein at least two bores for guiding the angle of entry into a first cortical plate of the jawbone of a subject, of a tool employed for forming lateral bores through which said implant anchor is to be placed so as to interlock with said dental implant while simultaneously engaging a tissue of the first and second cortical plates of the jawbone.

15. The multi-cortical self-locking dental implant kit of claim 14, and wherein said bridge member has formed thereon an outward-facing index member, and said second template portion has formed therein an indexing recess, said index member and said indexing recess being operative for mating engagement so as to position said at least one bore formed in said implant guide in a predetermined position relative to said implant anchor so that said implant anchor is located so as to receive said dental implant therein.

16. The multi-cortical self-locking dental implant kit of claim 14, and wherein said implant positioning template includes means for selectably adjusting the position of said first and second guide portions with respect to each other.

17. The multi-cortical self-locking dental implant kit of claim 14, wherein said template also includes means for adjusting the height of said implant positioning template with respect to the jawbone of the subject, at the site for the placement of said dental implant.

18. The multi-cortical self-locking dental implant kit of claim 17, wherein said means for adjusting the height of said implant positioning template includes spacers adapted to be disposed between said first guide portion and the jawbone.

19. The multi-cortical self-locking dental implant kit of claim 18, wherein said template further comprises a third guide portion, connected to said first guide portion and generally parallel to said second guide portion, and wherein said second and third guide portions are adapted for seating about the jawbone at the site of the dental implant, so as to assist in the centering thereof of said at least one bore of said first guide portion.

20. A method of mounting the implant device of claim 1 comprising:
providing the implant device of claim 1;
providing a socket in the jawbone for the implant;
inserting the elongate members via a pair of holes in one cortical plate of the jawbone on one side of the socket, through a socket in the jawbone and through a second pair of holes on a cortical plate on an opposite side of the socket, such that a portion of the elongate members is within the socket;
inserting the dental implant into the jawbone and engaging the grippable region with the elongate members.

21. A method according to claim 20 wherein when the elongate members are inserted into the jawbone and engaged by the dental implant, the bridge member remains outside the socket.

22. A method according to claim 21 wherein, when the distance between said elongate members of the said anchor is less than the thickness of said elongate shank of the dental implant prior to engagement therebetween, the distance between said elongate members increases upon the insertion of said dental implant at the area of engagement of the said elongate shank with said elongate members of the anchor.

23. An implant device, comprising:
a dental implant having a generally elongate shank and a grippable region formed at a predetermined portion thereof;
and an anchor including a first elongate member and a second elongate member connected by a bridge member,
said first elongate member and said second elongate member having inner confronting surfaces spaced from each other and constructed to lockably engage said grippable region of said dental implant against movement with respect to said anchor, with said elongate members extending transversely across said elongate shank,
wherein each of said first elongate member and said second elongate member has first and second ends dimensioned to simultaneously engage a tissue of a first cortical plate of the jawbone and a tissue of a second cortical plate of the jawbone, respectively, while lockably engaging said grippable region of said dental implant against movement with respect to said anchor, and wherein a coronal end portion of the dental implant is in a position which enables mounting a prosthesis thereon.

24. An implant device according to claim 23 wherein the elongate shank at the grippable region has an extent in the direction between the elongate members that is greater than the distance between the elongate members.

* * * * *